US009980718B2

(12) United States Patent
Housman et al.

(10) Patent No.: US 9,980,718 B2
(45) Date of Patent: May 29, 2018

(54) THREADED SUTURE ANCHOR

(71) Applicant: Smith & Nephew, Inc., Memphis, TN (US)

(72) Inventors: Mark Edwin Housman, North Attleborough, MA (US); Paul Steven Vincuilla, North Attleborough, MA (US); Richard M. Lunn, Kingston, MA (US); Julie Kennelly Tripodi, Marlborough, MA (US); Paul Leo Salvas, East Bridgewater, MA (US); Roland Francis Gatturna, Bourne, MA (US)

(73) Assignee: Smith & Nephew, Inc., Memphis, TN (US)

( * ) Notice: Subject to any disclaimer, the term of this patent is extended or adjusted under 35 U.S.C. 154(b) by 143 days.

(21) Appl. No.: 15/256,954

(22) Filed: Sep. 6, 2016

(65) Prior Publication Data

US 2016/0374661 A1 Dec. 29, 2016

Related U.S. Application Data

(62) Division of application No. 15/138,885, filed on Apr. 26, 2016, now Pat. No. 9,642,611, which is a division
(Continued)

(51) Int. Cl.
*A61B 17/04* (2006.01)
*A61B 17/86* (2006.01)
(Continued)

(52) U.S. Cl.
CPC ...... *A61B 17/0401* (2013.01); *A61B 17/0469* (2013.01); *A61B 17/861* (2013.01);
(Continued)

(58) Field of Classification Search
CPC ............ A61B 17/0469; A61B 17/0401; A61B 2017/0409; A61B 17/861; A61B 17/1655;
(Continued)

(56) References Cited

U.S. PATENT DOCUMENTS 5,100,417 A * 3/1992 Cerier ................ A61B 17/0401
606/139
5,156,616 A * 10/1992 Meadows .......... A61B 17/0401
411/395
(Continued)

FOREIGN PATENT DOCUMENTS

JP 2008515605 A 5/2008
JP 2008535544 A 9/2008
(Continued)

OTHER PUBLICATIONS

Chinese Office Action from corresponding International Application No. 201510469654.3, dated Jan. 4, 2018.
(Continued)

*Primary Examiner* — Son Dang
(74) *Attorney, Agent, or Firm* — Burns & Levinson, LLP; Joseph M. Maraia

(57) ABSTRACT

The present disclosure relates to a suture anchor. The suture anchor includes a body having a proximal end and a distal end, the body including threads along at least a partial length of the body and at least one through hole, the threads including a profile such that the threads located near the distal end of the body include a first shape and the threads located near the proximal end of the body include a second shape different from the first shape. Delivery devices and anchor dilators are also disclosed.

8 Claims, 18 Drawing Sheets

Related U.S. Application Data of application No. 12/914,129, filed on Oct. 28, 2010, now Pat. No. 9,393,006.

(60) Provisional application No. 61/255,508, filed on Oct. 28, 2009, provisional application No. 61/255,509, filed on Oct. 28, 2009, provisional application No. 61/255,510, filed on Oct. 28, 2009, provisional application No. 61/255,511, filed on Oct. 28, 2009, provisional application No. 61/297,418, filed on Jan. 22, 2010, provisional application No. 61/309,643, filed on Mar. 2, 2010, provisional application No. 61/307,980, filed on Feb. 25, 2010, provisional application No. 61/311,841, filed on Mar. 9, 2010, provisional application No. 61/324,966, filed on Apr. 16, 2010, provisional application No. 61/359,084, filed on Jun. 28, 2010.

(51) Int. Cl.
*A61B 17/16* (2006.01)
*A61B 17/88* (2006.01)

(52) U.S. Cl.
CPC ...... *A61B 17/8645* (2013.01); *A61B 17/1655* (2013.01); *A61B 17/863* (2013.01); *A61B 17/8875* (2013.01); *A61B 17/8877* (2013.01); *A61B 2017/044* (2013.01); *A61B 2017/0409* (2013.01); *A61B 2017/0414* (2013.01); *A61B 2017/0445* (2013.01)

(58) Field of Classification Search
CPC ........ A61B 2017/0445; A61B 17/8877; A61B 2017/0414; A61B 17/8645; A61B 17/863; A61B 17/8875; A61B 2017/044
See application file for complete search history.

(56) References Cited

U.S. PATENT DOCUMENTS

| | | | | |
|---|---|---|---|---|
| 5,217,462 A * | 6/1993 | Asnis | ...................... | A61B 17/74 606/105 |
| 5,733,307 A * | 3/1998 | Dinsdale | ............ | A61B 17/0401 606/104 |
| 5,743,914 A * | 4/1998 | Skiba | ................. | A61B 17/8625 411/412 |
| 5,899,920 A * | 5/1999 | DeSatnick | ......... | A61B 17/0401 606/232 |
| 5,925,048 A * | 7/1999 | Ahmad | .............. | A61B 17/8605 606/308 |
| 6,036,491 A * | 3/2000 | Hansson | ............ | A61B 17/8625 433/174 |
| 6,048,344 A * | 4/2000 | Schenk | ................... | A61B 17/68 606/304 |
| 6,355,043 B1 * | 3/2002 | Adam | .................... | A61B 17/72 470/27 |
| 6,517,542 B1 * | 2/2003 | Papay | ................ | A61B 17/0401 606/232 |
| 7,179,260 B2 * | 2/2007 | Gerlach | ............ | A61B 17/8014 606/291 |
| 2004/0106950 A1 * | 6/2004 | Grafton | .............. | A61B 17/0401 606/232 |
| 2006/0276841 A1 * | 12/2006 | Barbieri | ............. | A61B 17/0401 606/232 |
| 2007/0203498 A1 * | 8/2007 | Gerber | ............... | A61B 17/0401 606/328 |
| 2008/0147063 A1 * | 6/2008 | Cauldwell | .......... | A61B 17/0401 606/60 |
| 2008/0306511 A1 * | 12/2008 | Cooper | ............... | A61B 17/0401 606/232 |
| 2009/0076545 A1 * | 3/2009 | DiMatteo | ........... | A61B 17/0401 606/232 |
| 2009/0082807 A1 * | 3/2009 | Miller | ................. | A61B 17/0401 606/232 |
| 2009/0234387 A1 * | 9/2009 | Miller | ................ | A61B 17/0401 606/232 |
| 2010/0016869 A1 * | 1/2010 | Paulk | .................. | A61B 17/0401 606/144 |
| 2010/0016902 A1 * | 1/2010 | Paulk | .................. | A61B 17/0401 606/300 |
| 2010/0152773 A1 * | 6/2010 | Lunn | .................. | A61B 17/0401 606/232 |
| 2010/0217332 A1 * | 8/2010 | Daniels | .............. | A61B 17/8057 606/305 |

FOREIGN PATENT DOCUMENTS

| | | |
|---|---|---|
| JP | 2013509257 A | 3/2013 |
| WO | 2006044491 A2 | 4/2006 |
| WO | 2006099109 A2 | 9/2006 |
| WO | 2011056701 A1 | 5/2011 |

OTHER PUBLICATIONS

Office Action from related Japanese Application No. 2016-015657 datd Oct. 24, 2016.

\* cited by examiner

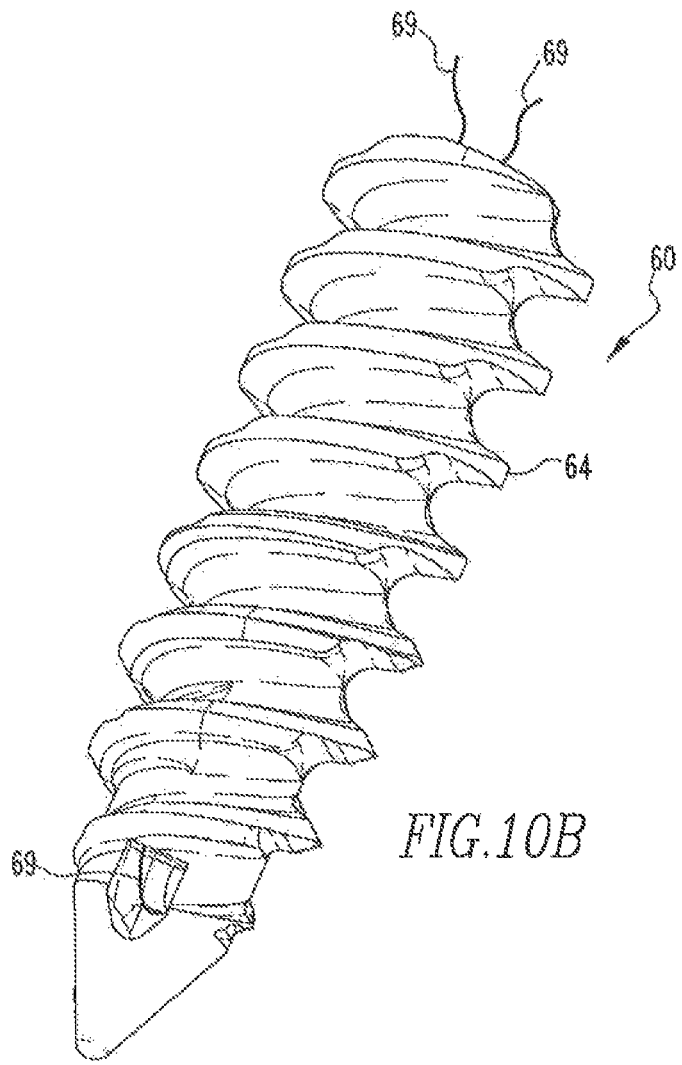

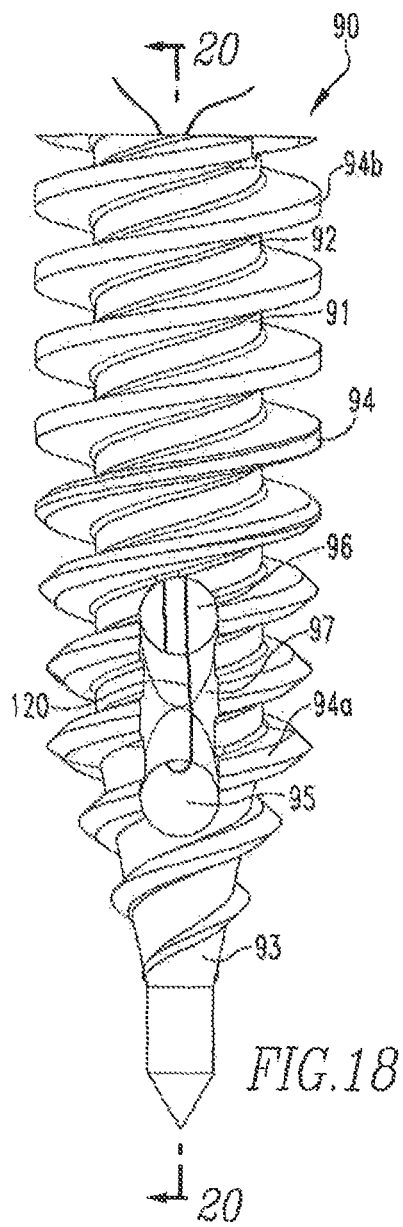
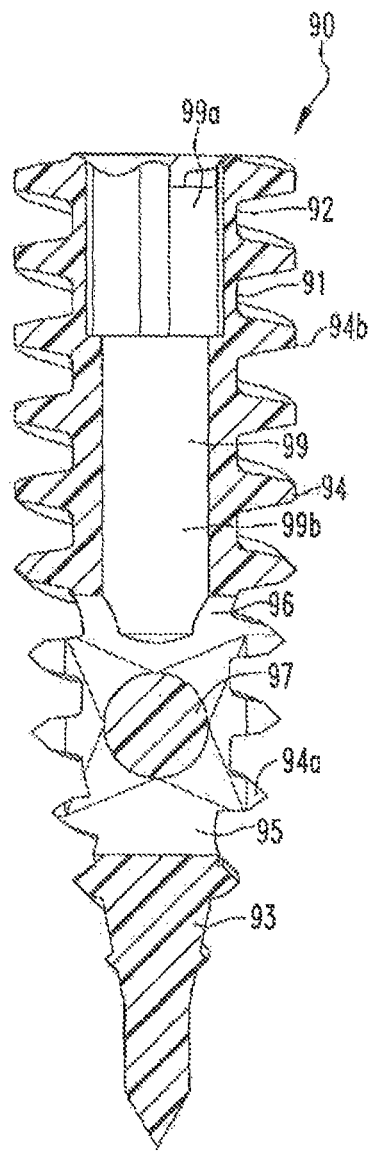
FIG.18
FIG.19

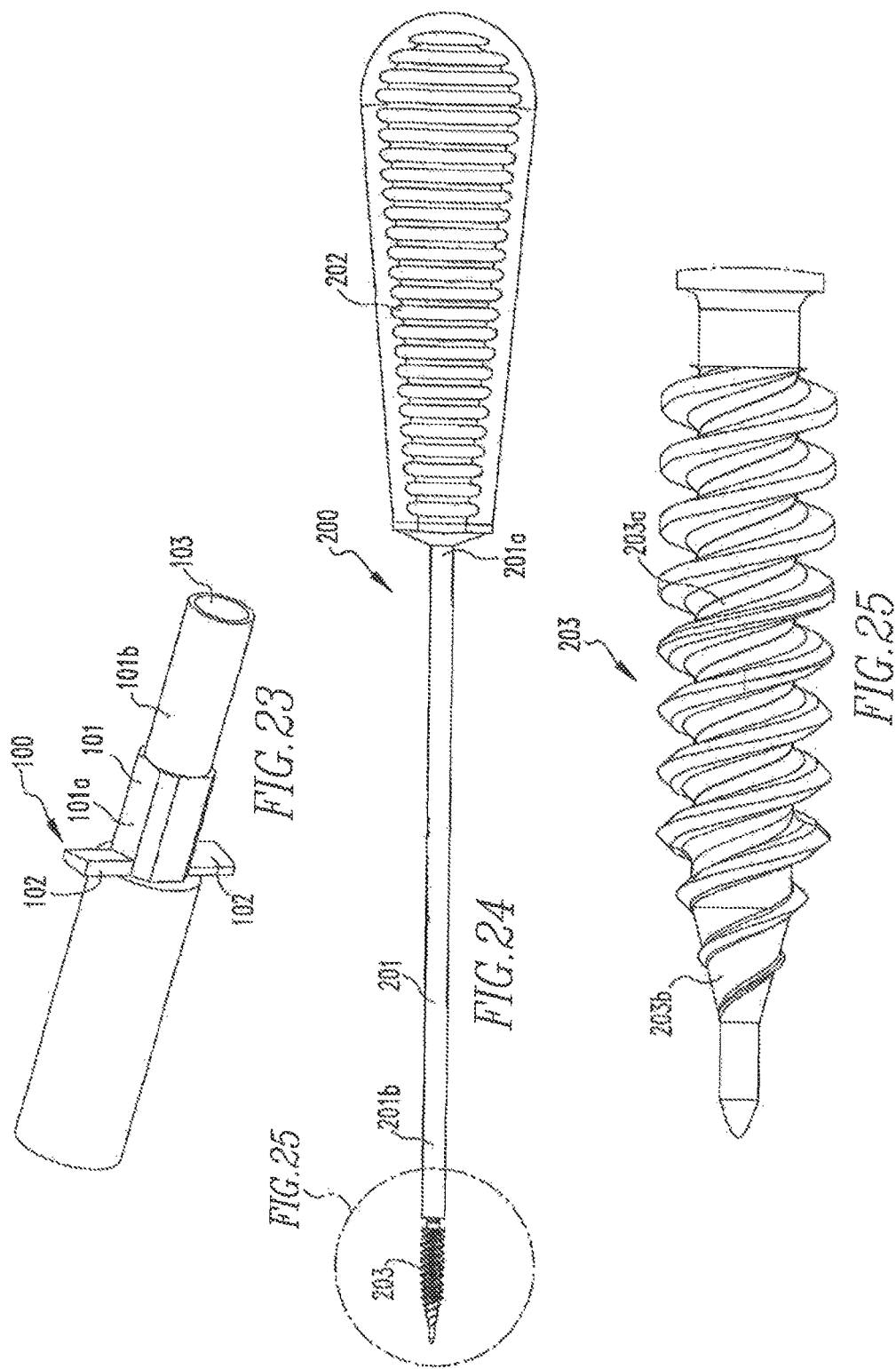

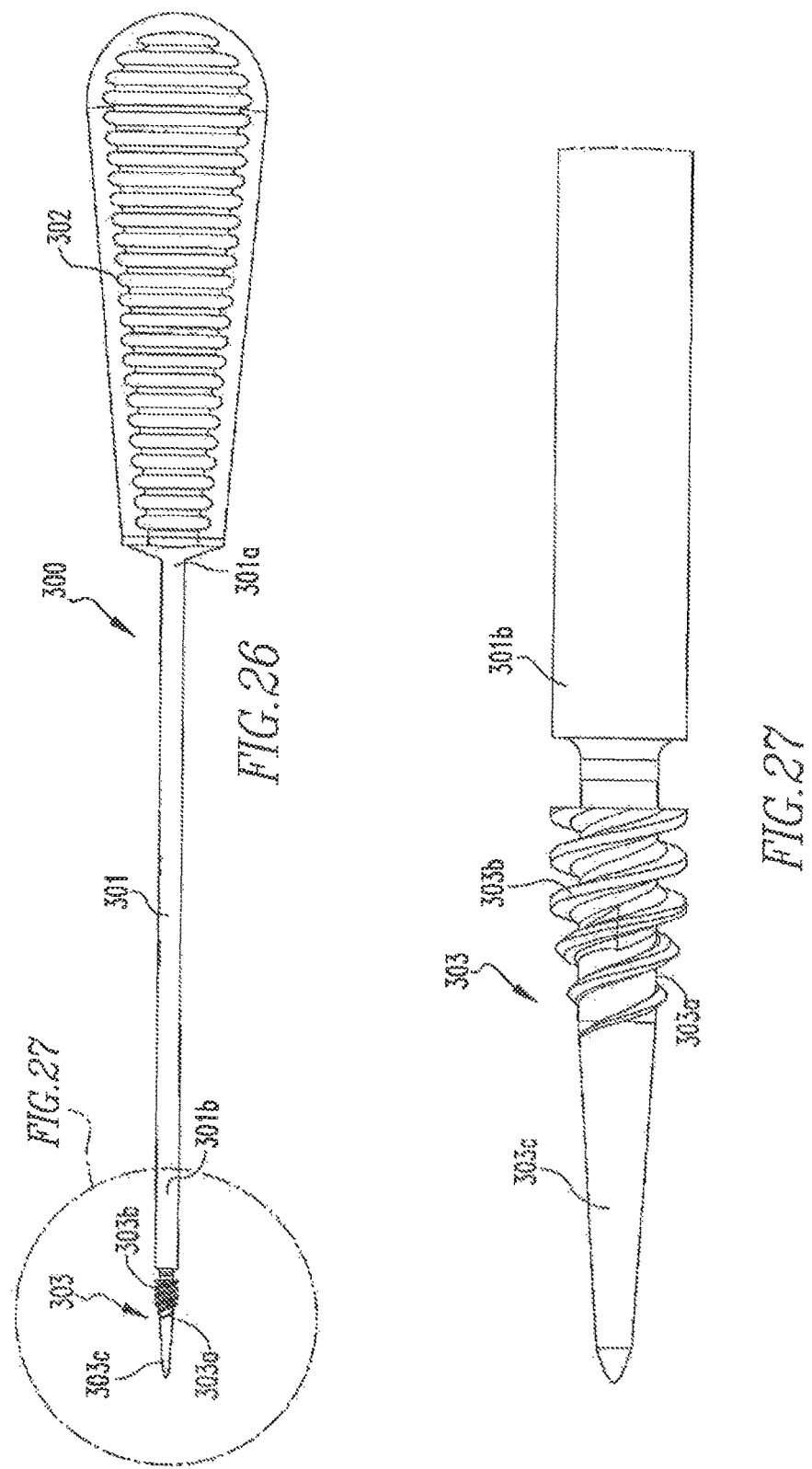

THREADED SUTURE ANCHOR

CROSS REFERENCE TO RELATED APPLICATIONS

This application is a divisional of co-pending U.S. patent application Ser. No. 15/138,885, filed Apr. 26, 2016, entitled THREADED SUTURE ANCHOR, which in turn is a divisional of U.S. patent application Ser. No. 12/914,129, filed Oct. 28, 2010, which in turn claims priority to and benefit of U.S. Patent Application No. 61/255,508, filed Oct. 28, 2009, U.S. Patent Application No. 61/255,509, filed Oct. 28, 2009, U.S. Patent Application No. 61/255,510, filed Oct. 28, 2009, U.S. Patent Application No. 61/255,511, filed Oct. 28, 2009, U.S. Patent Application No. 61/297,418, filed Jan. 22, 2010, U.S. Patent Application No. 61/309,643, filed Mar. 2, 2010, U.S. Patent Application No. 61/307,980, filed Feb. 25, 2010, U.S. Patent Application No. 61/311,841, filed Mar. 9, 2010, U.S. Patent Application No. 61/324,966, Apr. 16, 2010, and U.S. Patent Application No. 61/359,084, filed Jun. 28, 2010, the disclosures of which are incorporated herein by reference in their entireties for all purposes.

BACKGROUND

Field of Technology

The present disclosure relates to the repair of soft tissue and, specifically, devices for use in such repair.

Related Art

Arthroscopic procedures often require soft tissue to be reattached to bone. To achieve this, anchors are placed in the bone and sutures attached to the anchor are passed through the tissue to securely retain the tissue in place. When making a repair of soft tissue to bone, it is advantageous for the suture anchor and the anchor inserter to have features that allow for ease of insertion and increased fixation of the anchor to the bone. A procedure, and devices for use in such procedure, that securely attaches tissue to bone is needed.

SUMMARY

In an aspect, the present disclosure relates to a suture anchor. The suture anchor includes a body having a proximal end and a distal end, the body including threads along at least a partial length of the body and at least one through hole, the threads including a profile such that the threads located near the distal end of the body include a first shape and the threads located near the proximal end of the body include a second shape different from the first shape.

In another aspect, the present disclosure relates to a delivery device. The device includes a square-shaped end including two prongs extending from the end, the prongs located at opposite corners of the end, wherein the device is cannulated.

In yet another aspect, the present disclosure relates to a delivery device. The device includes an end having a first area and a second area, wherein the first area is of a first shape and the second area is of a second shape different from the first shape, the first shape and the second shape including different diameters, the device being cannulated.

In a further aspect, the present disclosure relates to a delivery device. The device includes an end having a first area and a second area wherein the first area is of a first shape and the second area is of a second shape different from the first shape, the first shape and the second shape including different diameters, the device being cannulated, wherein one of the areas includes tangs extending outwardly from the device.

In yet a further aspect, the present disclosure relates to an anchor dilator. The dilator includes a handle; a shaft coupled to the handle; and a dilating portion coupled a distal end of the shaft, the dilating portion including a body having threads, the threads including a profile such that the threads located near the distal end of the body include a first shape and the threads located near the proximal end of the body include a second shape different from the first shape.

In an aspect, the present disclosure relates to an anchor dilator. The anchor dilator includes a handle; a shaft coupled to the handle; and a dilating portion coupled to a distal end of the shaft, the dilating portion including a body having a threaded first portion and a non-threaded second portion, the threaded first portion including a profile such that threads located near a distal end of the body include a first shape and threads located near a proximal end of the body include a second shape different from the first shape.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIGS. 10A and 10B show a side view and an isometric view of an alternative embodiment of the suture anchor of the present disclosure.

FIG. 18 shows a side view of yet another alternative embodiment of the suture anchor of the present disclosure.

FIG. 19 shows a cross-sectional view of the suture anchor of FIG. 18.

FIG. 23 shows an isometric view of the distal end of the delivery device of FIG. 21.

FIG. 24 shows a side view of an anchor dilator for use with the suture anchors of the present disclosure during tissue repair.

FIG. 25 shows a side view of the distal end of the anchor dilator of FIG. 24.

FIG. 26 shows a side view of an alternative embodiment of the anchor dilator of the present disclosure.

FIG. 27 shows an enlarged view of the distal end of the anchor dilator of FIG. 26.

DETAILED DESCRIPTION OF THE EMBODIMENTS

Figure 1:
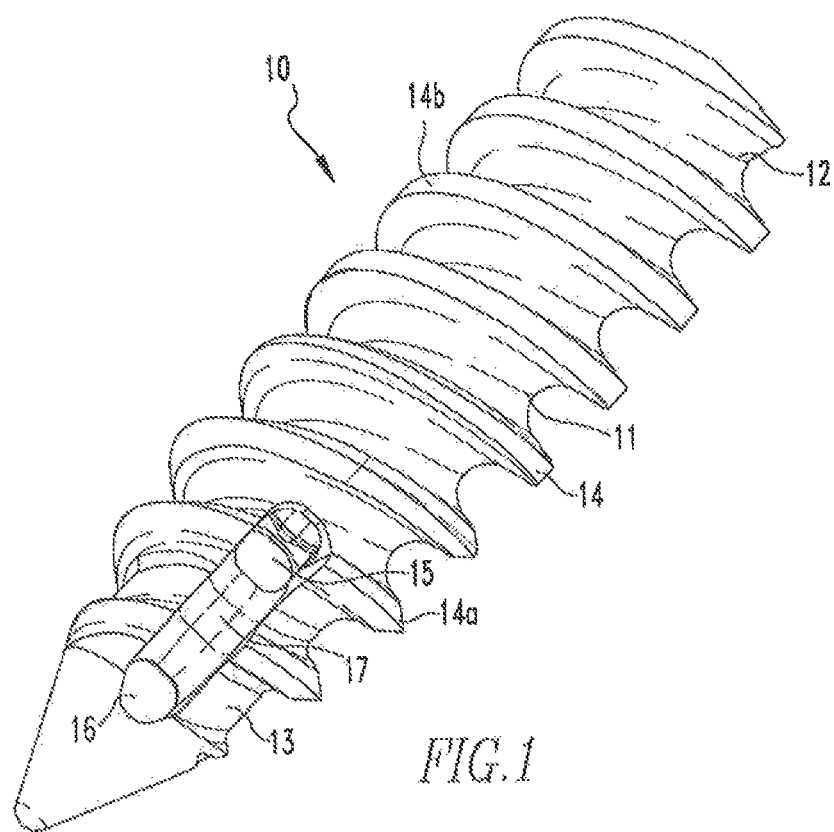
FIG. 1 shows an isometric view of the suture anchor of the present disclosure without suture.

The following description of the preferred embodiment(s) is merely exemplary in nature and is in no way intended to limit the disclosure, its application, or uses.

FIGS. 1-4 show the threaded suture anchor 10 of the present disclosure. The anchor 10 includes a body 11 having a proximal end 12 and a distal end 13. The body 11, is tapered from the proximal end 12 to the distal end 13 such that the distal end 13 is pointed. The anchor 10 is threaded along at least a partial length of the body 11 such that a portion of the distal end 13 is not threaded. The threads 14 have a profile such that the threads 14a at the distal end 13 have a sharper, cutting shape and the threads 14b at the proximal end 12 have a square shape. The purpose for this transitional thread profile will be further described below. The anchor 10 also includes two through holes 15,16 and a bridge 17 located between the holes 15,16. The bridge 17 is of a size that interrupts the least number of threads 14.

Figures 3, 4:
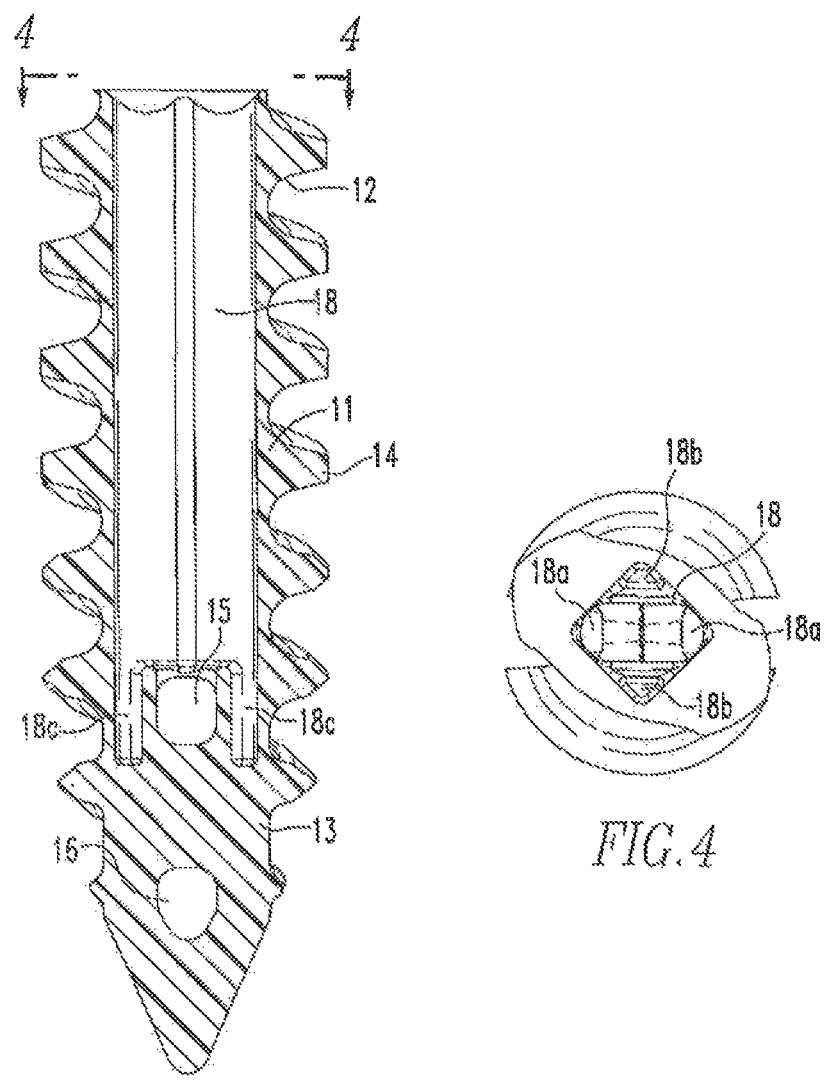
FIG. 3 shows a cross-sectional view of the suture anchor of FIG. 1.
FIG. 4 shows a top view of the suture anchor of FIG. 1.

As shown more clearly in FIGS. 3 and 4, the anchor 10 also includes a cannulation 18. The cannulation 18 has a square shape such that at least two of its corners 10a are aligned with through holes 15,16 and two of its corners 18b are not aligned with through holes 15,16, as shown more clearly in FIG. 4. The cannulation 18 extends though the anchor 10 such that a portion of the cannulation 18 extends around through hole 15 to form slots 18c that will be used to house a portion of the anchor inserter, as will be further described below. The slots 18c are aligned with corners 18b of the cannulation.

Figure 2:
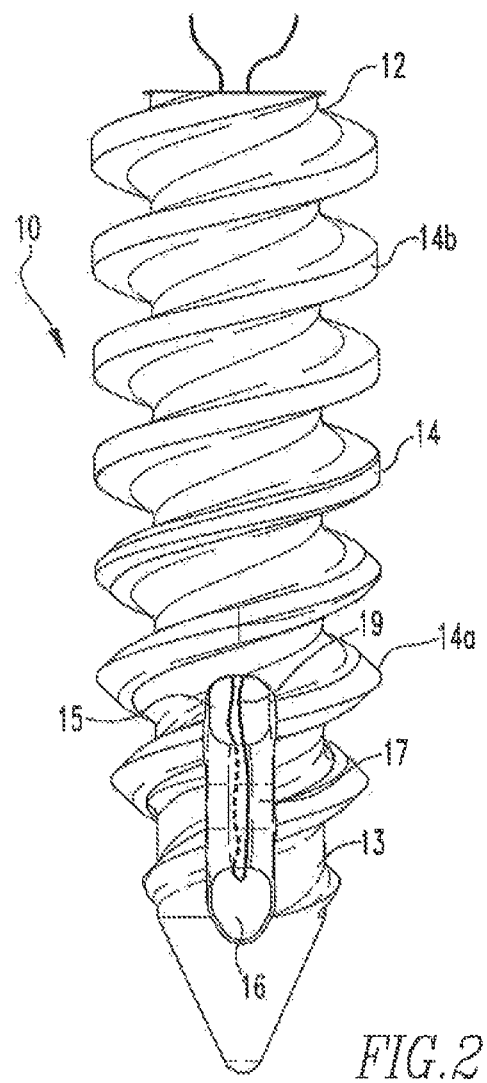
FIG. 2 shows a side elevational view of the suture anchor of FIG. 1 with suture.

As shown in FIG. 2, a flexible member 19, such as a suture, extends around the bridge 17 and through the cannulation 18, via the corners 18a of the cannulation 18 that are aligned with the through holes 15,16.

Figure 5:
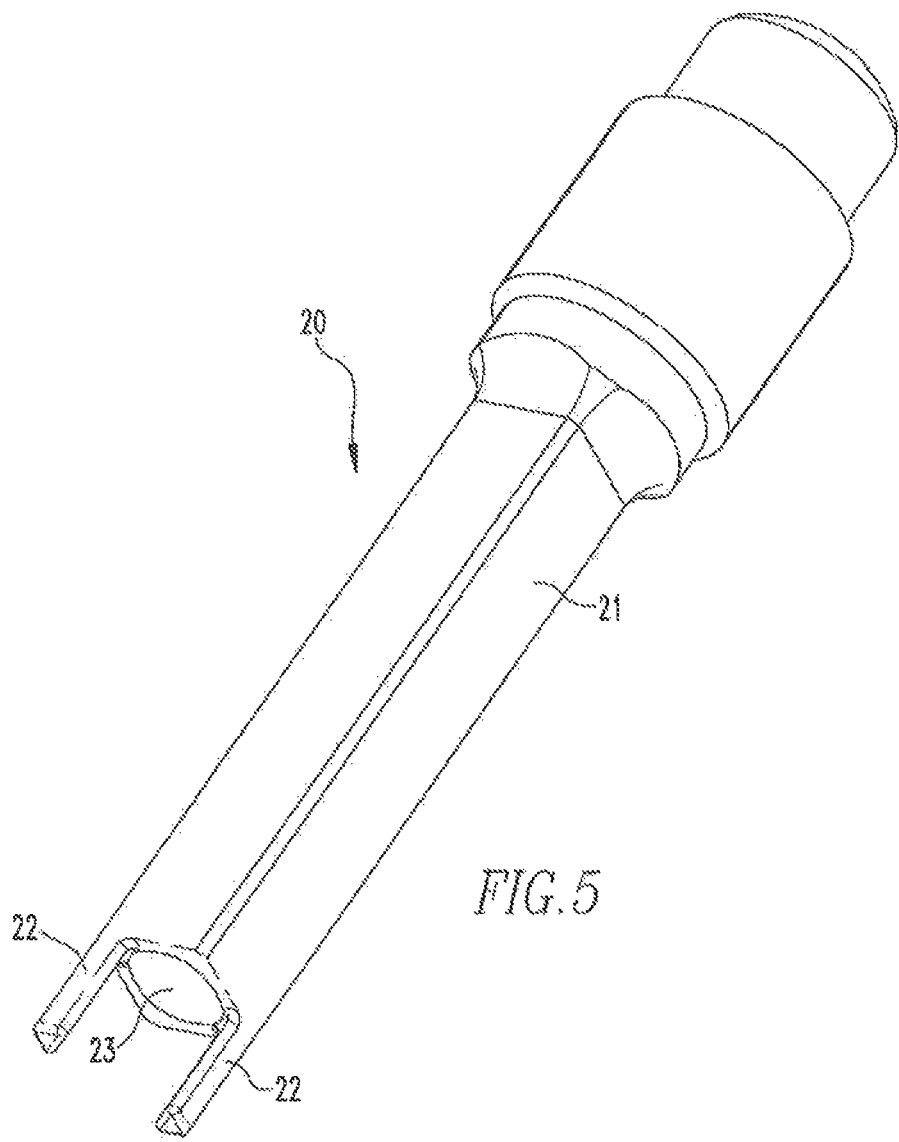
FIG. 5 shows an isometric view of a distal end of the suture anchor inserter of the present disclosure.
Figure 6:
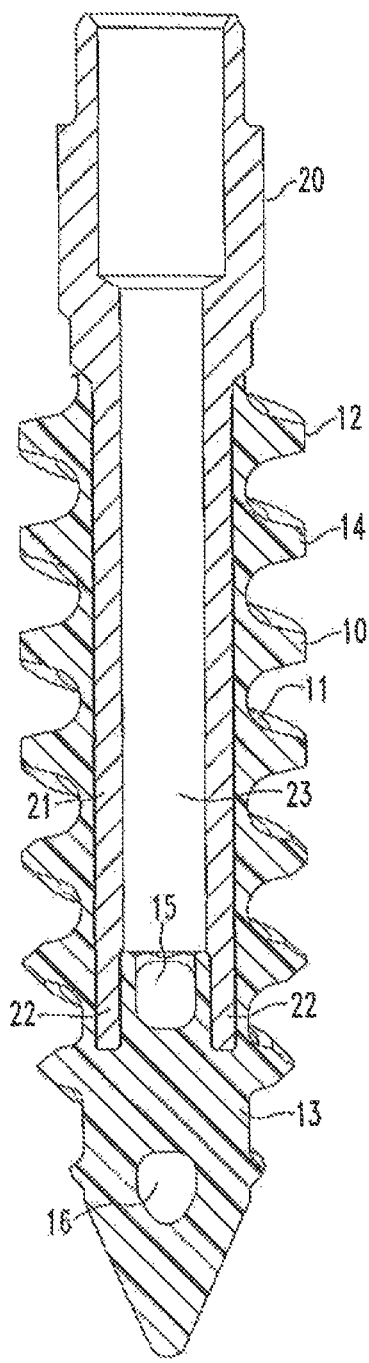
FIG. 6 shows a cross-sectional view of the suture anchor assembly of the present disclosure without suture.
Figure 7:
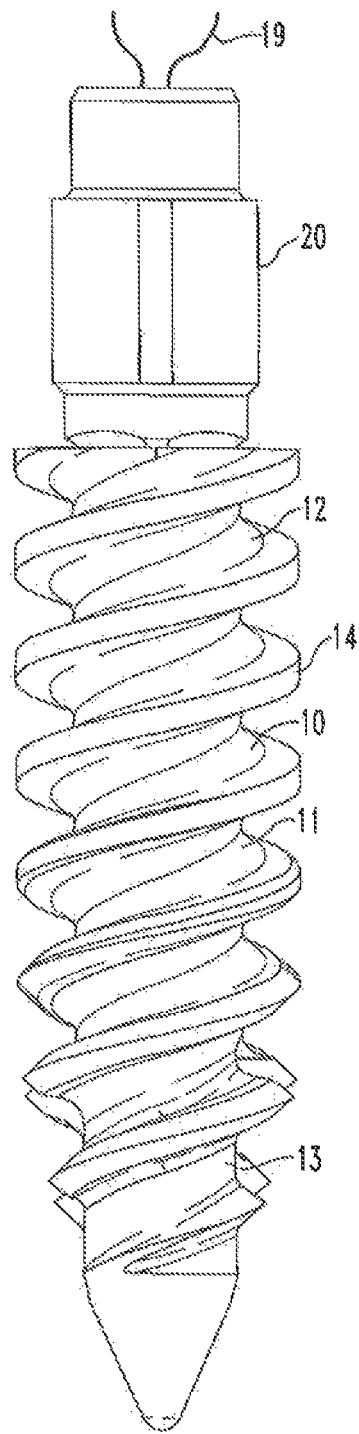
FIG. 7 shows a side elevational view of the of the suture anchor assembly of FIG. 6 with suture.

FIG. 5 shows a distal end 21 of the anchor inserter 20. The end 21 is square-shaped to correspond with the square-shaped cannulation 18 when the end 21 is housed within the cannulation 18, as shown in FIGS. 6 and 7. Additionally, two prongs 22 extend from the distal end 21. These two prongs 22 are configured for housing in the slots 18c of the cannulation 18, as more clearly shown in FIG. 6. Housing of the prongs 22 in the slots 18c provides the inserter 20 with a higher insertion torque during advancement of the anchor 10 into bone, as will be further described below. The anchor inserter 20 is cumulated such that when the end 21 is housed within the cannulation 18, the suture 19 extends through the cannulation 23 of the inserter 20. The corners 18a maximize the cross-sectional area available for the suture 19 to pass through from the bridge 17 and up through the driver cannulation 23.

Figure 8:
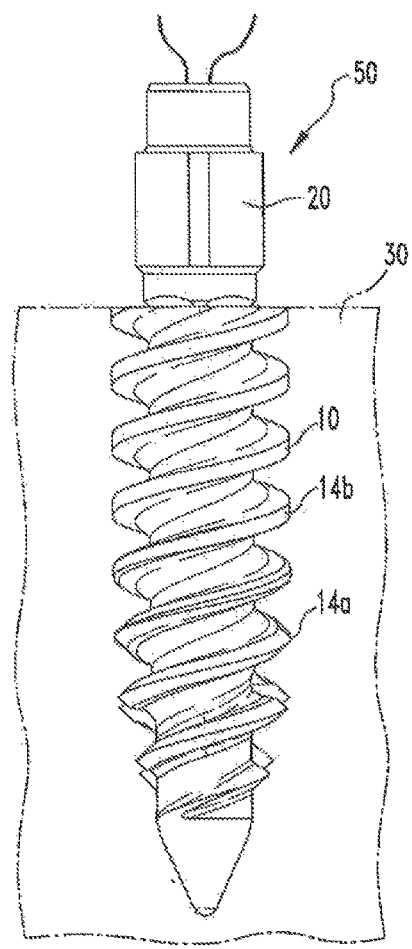
FIGS. 8-9 show a method of soft tissue repair using the suture anchor and suture anchor assembly of FIGS. 1 and 7.
Figure 9:
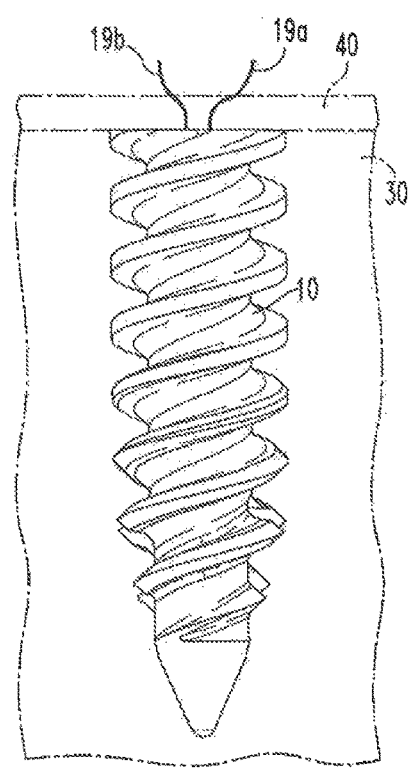

FIGS. 8 and 9 show the suture anchor assembly 50 (anchor 10 and inserter 20) of the present disclosure during use in the repair of tissue. The anchor 10 is inserted into a previously drilled hole in the bone 30 and rotated until the entire anchor 10 is located in the bone 30, as shown in FIG. 8. During initial insertion of the anchor 10, the cutting threads 14a help ease introduction of the anchor 10 into the bone by cutting through the bone 30. As rotation of the anchor 10 continues and the thread profile begins to change from the cutting threads 14a to the square-shaped threads 14b, an increased amount of interference occurs between the threads 14 and the bone 30, which causes an increase in torsion resistance. This increase in torsion resistance allows the anchor 10 to be firmly affixed in the bone 30 and substantially reduces the possibility of the anchor 10 from backing out of the bone 30.

Once the anchor 10 has been inserted into the bone 30, the inserter 20 is removed from the anchor 10 and soft tissue 40 is placed adjacent to the anchor 10, as shown more clearly in FIG. 9. Ends 19a,19b of the suture 19 are inserted through the soft tissue 40 and tied to fixate the tissue 40 to the bone.

Figure 10A:
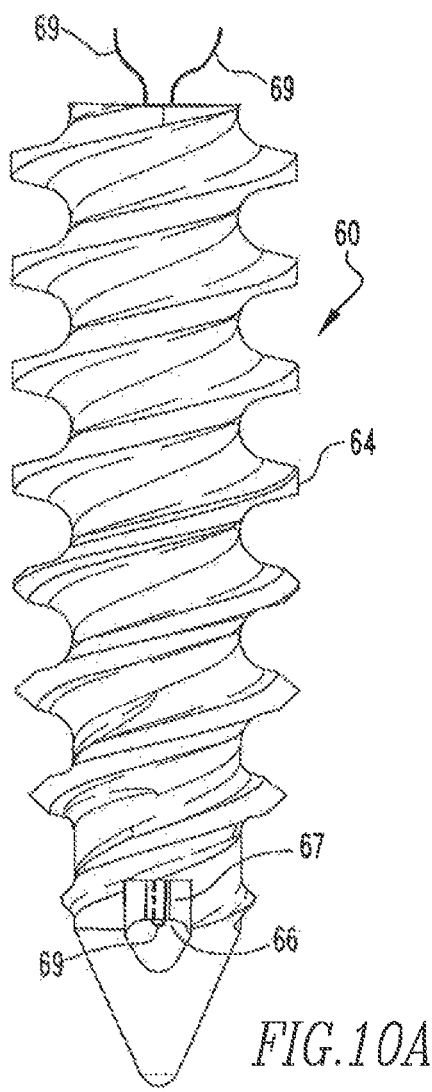
Figures 11, 12:
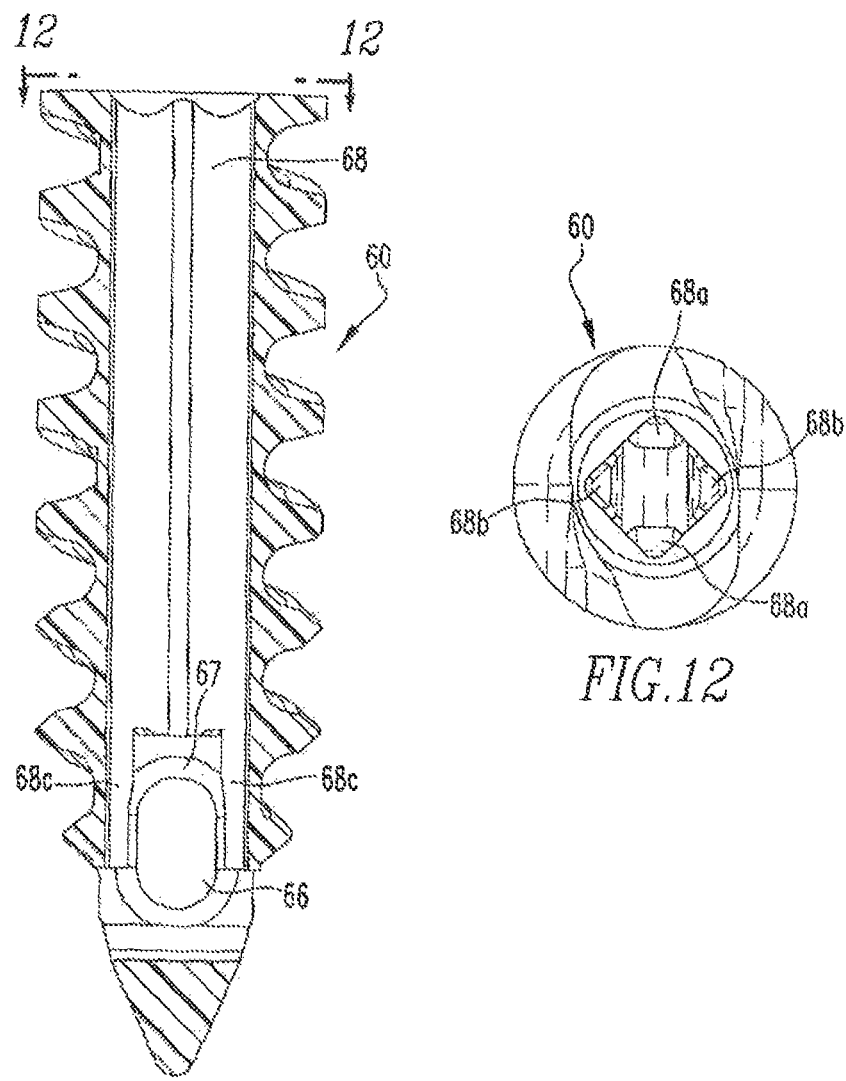
FIG. 11 shows a cross-sectional view of the suture anchor of FIG. 10.
FIG. 12 shows a top view of the suture anchor of FIG. 10.

FIGS. 10A and 10B show alternative embodiments of the suture anchor 60 of the present disclosure. Suture anchor 60 is similar to suture anchor 10 except suture anchor 60 doesn't include two through holes. Rather, suture anchor 60 includes only one through hole 66. Having a single through hole allows for even less interruption of the number of threads 64. As shown more clearly in FIGS. 11 and 12, similar to anchor 10, anchor 60 also includes a cannulation 68 having a square shape such that at least two of its corners 68a are aligned with through hole 66 and two of its corners 68b are not aligned with through hole 66, as shown more clearly in FIG. 12. The cannulation 68 extends though the anchor 60 such that a portion of the cannulation 68 extends around the bridge 67 to form slots 68c that will be used to house a portion of the anchor inserter, as described above. The slots 68c are aligned with corners 68b of the cannulation.

As shown in FIGS. 10A and 10B, a flexible member 69, such as a suture, extends around the bridge 67 and through the cannulation 68, via the corners 68a of the cannulation 68 that are aligned with the through hole 66. The anchor inserter 20 of FIG. 5 is used to insert the anchor 60 into bone during tissue repair, similar to the manner in which the inserter 20 is used with suture anchor 10, as described above.

Other alternative features/embodiments are also within the scope of this disclosure. The distal ends of the anchors in FIGS. 1-10 may be fully threaded. The thread shapes at the proximal ends of the anchors may be any shape that would allow for an increased amount of interference between the threads and the bone. The number of through holes may be less or more than two and they may be located anywhere along the lengths of the anchors. The cannulations of the anchors may be of any shapes that would maximize the cross-sectional areas available for the sutures to pass through from the bridges and up through the driver cannulation. The number of sutures housed within each anchor may be more than one. In addition, flexible members other than sutures may be used.

The distal end of the inserter may include more or less than two prongs. Additionally, it is within the scope of this disclosure to have a distal end with prongs that do not straddle a through hole. The shape of the distal end of the driver may be other than square and therefore have more or less than four sides. The anchors are made from a non-metal material via an injection molding process. However, other material, which would allow the anchors to withstand the forces applied during surgery, and other processes may be used. Also, the driver is made from a metal material. However, other material that would allow the driver to withstand the forces applied during surgery may be used. Rather than drilling pilot holes into the bone and then inserting the anchors into the bone via the holes, the anchors may be inserted by tapping on the end of the inserter to advance the pointed distal ends of the anchors into the bone and then rotating the inserter to advance the rest of the anchors. Also, rather than tying the ends of the sutures to fixate the tissue, the tissue may be fixated to bone in another manner, such as by passing the ends through a second anchor and then placing the second anchor into the bone at another location.

Figure 13:
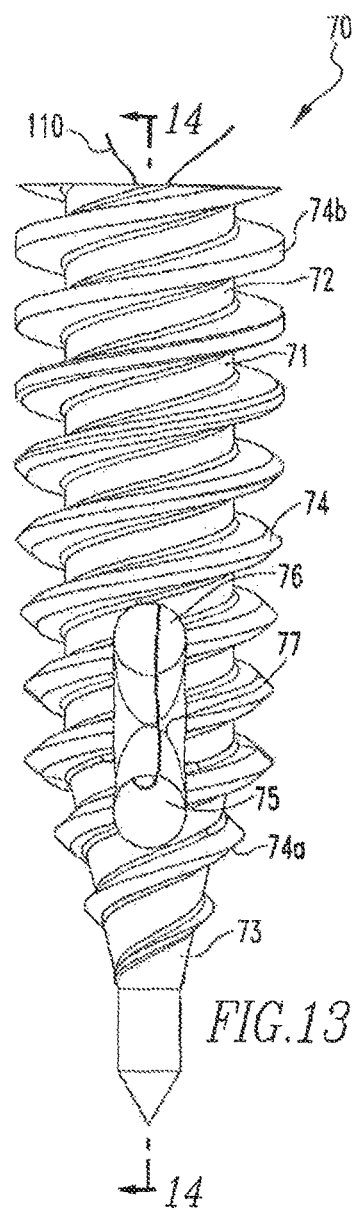
FIG. 13 shows a side view of another alternative embodiment of the suture anchor of the present disclosure.
Figure 14:
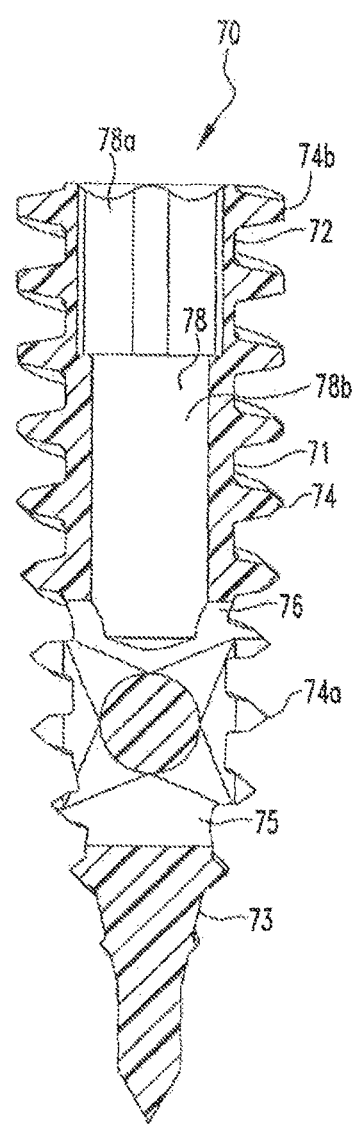
FIG. 14 shows a cross-sectional view of the suture anchor of FIG. 13.

FIGS. 13 and 14 show another alternative embodiment of the suture anchor 70 of the present disclosure. The anchor 70 includes a body 71 having a proximal end 72 and a distal end 73. The body 71 is tapered from the proximal end 72 to the distal end 73 such that the distal end 73 is pointed. Unlike the earlier embodiments, the distal end 73 is specifically designed to allow for insertion of the anchor 70 into bone without first creating a hole in the bone, as will be further described below. Similar to the earlier embodiments, the anchor 70 is threaded along at least a partial length of the body 71 such that a portion of the distal end 73 is not threaded. The threads 74 have a profile such that the threads 74a at the distal end 73 have a sharper, cutting shape and the threads 74b at the proximal end 72 have a square shape. The anchor 70 also includes two through holes 75,76 and a bridge 77 located between the holes 75,76. The bridge 77 is of a size that interrupts the least number of threads 74.

Figure 16:
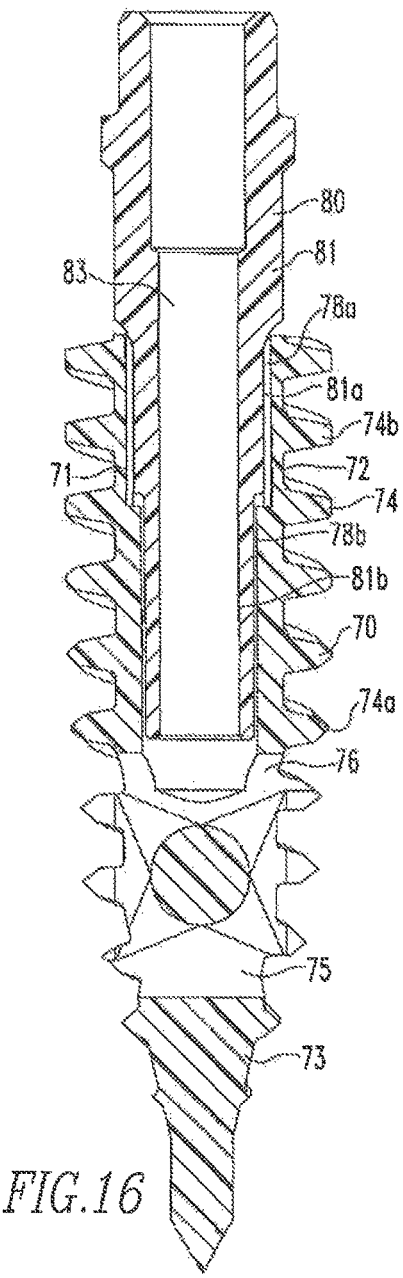
FIG. 16 shows a cross-sectional view of the suture anchor-delivery device of FIG. 15.
Figure 17:
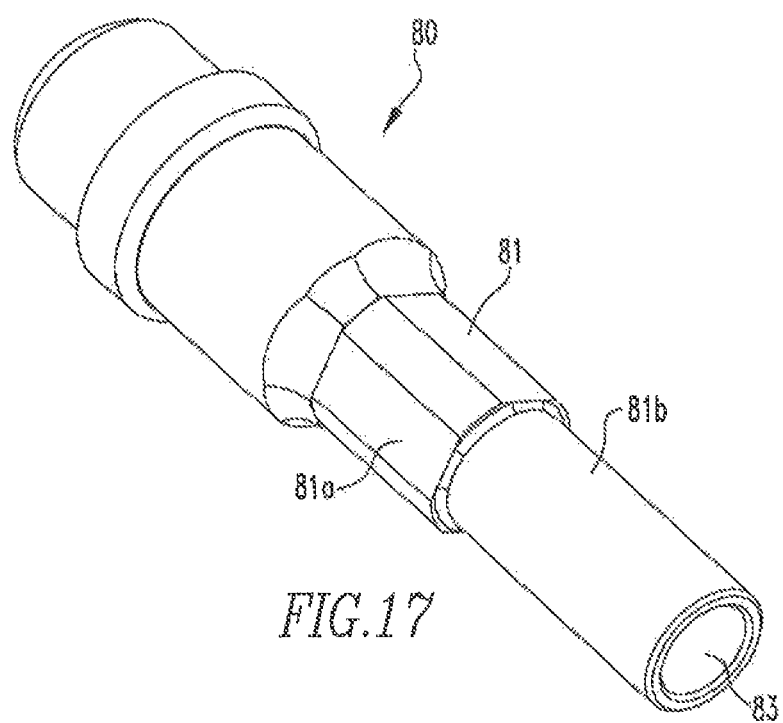
FIG. 17 shows an isometric view of a distal end of the delivery device of FIG. 15.

As shown more clearly in FIG. 14, the anchor 70 also includes a cannulation 78. The cannulation 78 includes two areas 78a,78b. Area 78a has a square shape and area 78b has a rounded or circular shape. Additionally, area 78a has a larger diameter than area 78b. The areas 78a,78b are designed to correspond to the design of the delivery device used to insert the anchor 70 into bone. For instance, FIG. 17 shows a distal end 81 of the delivery device 80 used to insert anchor 70 into bone. Similar to areas 78a,78b, the distal end 81 has a square-shaped area 81a and a rounded or circular-shaped area 81b. Also similar to areas 78a,78b, area 81 a has a larger diameter than area 81b. As shown in FIG. 16, once the distal end 81 is inserted into cannulation 78, the shape of area 78a corresponds with the shape of area 81a and the Shape of area 78b corresponds with the shape of area 81b. The shapes of the areas 78a,78b,81a,81b correspond with each other to allow for the proper amount of torque to be applied to the anchor 70 while the anchor 70 is being inserted into bone, as will be further described below.

Figure 20:
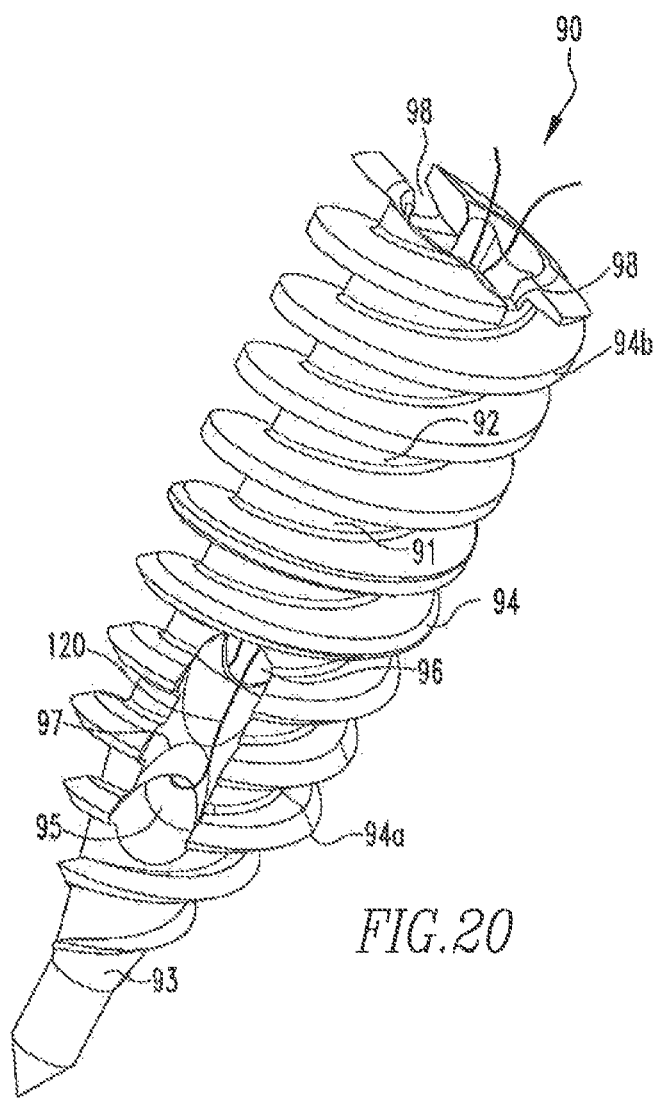
FIG. 20 shows an isometric view of the suture anchor of FIG. 18.

FIGS. 18-20 show yet another alternative embodiment of the suture anchor 90 of the present disclosure. Suture anchor 90 includes a body 91 having a proximal end 92 and a distal end 93. The body 91 is tapered from the proximal end 92 to the distal end 93 such that the distal end 93 is pointed. Similar to anchor 70, the distal end 93 is specifically designed to allow for insertion of the anchor 90 into bone without first creating a hole in the bone, as will be further described below. Also similar to the earlier embodiments, the anchor 90 is threaded along at least a partial length of the body 91 such that a portion of the distal end 93 is not threaded. The threads 94 have a profile such that the threads 94a at the distal end 93 have a sharper, cutting shape and the threads 94b at the proximal end 92 have a square shape. The anchor 90 also includes two through holes 95,96 and a bridge 97 located between the holes 95,96. The bridge 97 is of a size that interrupts the least number of threads 94. Additionally, as shown in FIG. 20, anchor 90 includes grooves 98, for purposes to be described later.

Figure 21:
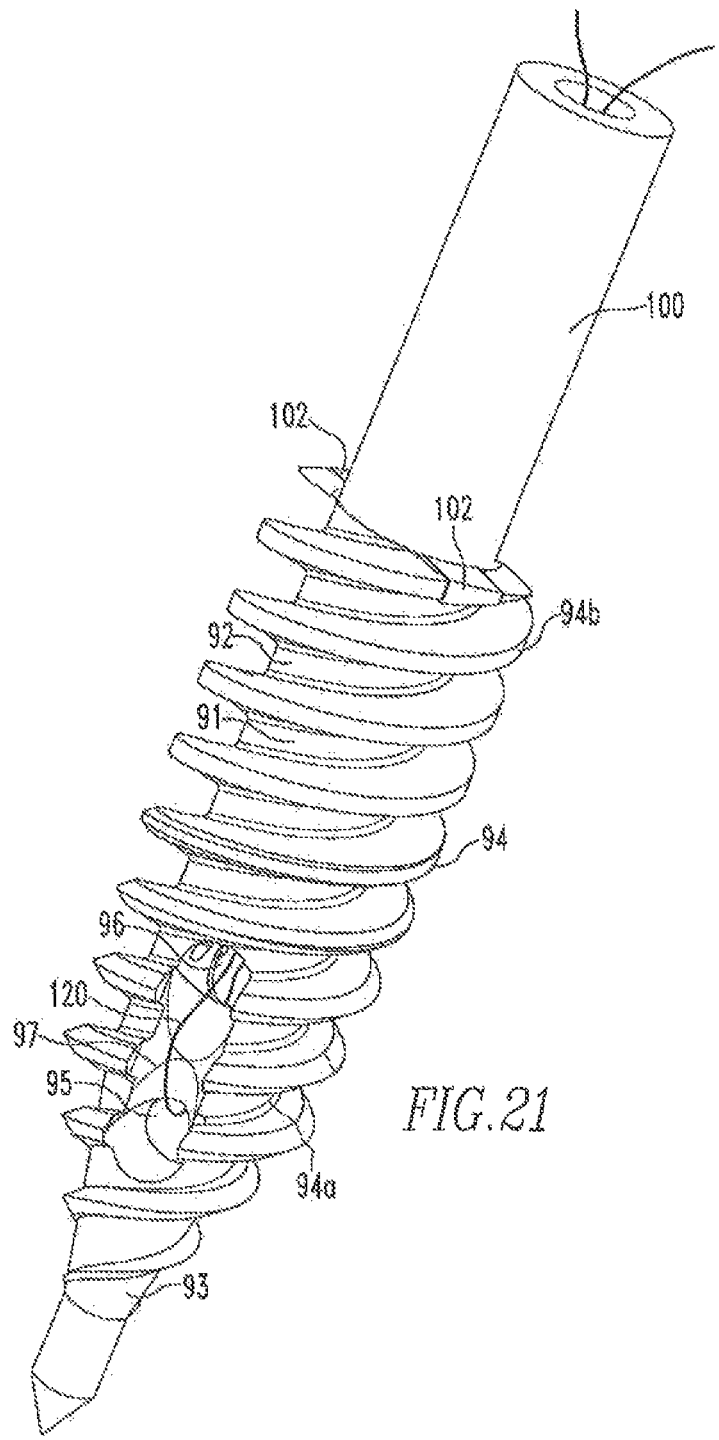
FIG. 21 shows an isometric view of the suture anchor of FIG. 18 and a delivery device coupled to the anchor.
Figure 22:
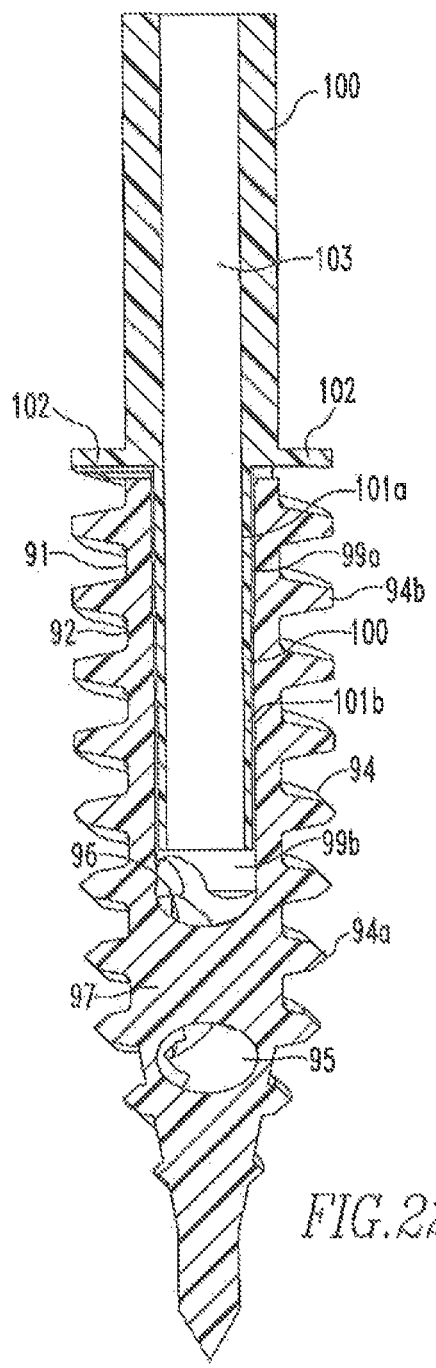
FIG. 22 shows a cross-sectional view of the suture anchor-delivery device of FIG. 21.

As shown more clearly in FIG. 19 and similar to anchor 70, the anchor 90 also includes a cannulation 99. The cannulation 99 includes two areas 99a,99b. Area 99a has a square shape and area 99b has a rounded or circular shape. Additionally, area 99a has a larger diameter than area 99b. The areas 99a,99b are designed to correspond to the design of the delivery device used to insert the anchor 90 into bone. For instance, FIG. 23 shows a distal end 101 of the delivery device 100 used to insert anchor 90 into bone. Similar to areas 99a,99b, the distal end 101 has a square-shaped area 101a and a rounded or circular-shaped area 101b. Also similar to areas 99a,99b, area 101a has a larger diameter than area 101b. Furthermore, the device 100 includes tangs 102 extending outwardly from the device 100. As shown in FIGS. 21 and 22, once the distal end 101 is inserted into cannulation 99, the shape of area 99a corresponds with the shape of area 101a and the shape of area 99b corresponds with the shape of area 101b. Also, the tangs 102 fit within the grooves 98. The shapes of the areas 99a,99b,101a,101b correspond with each other and the tangs 102 fit within the grooves 98 to allow for the proper amount of torque to be applied to the anchor 90 while the anchor 90 is being inserted into bone, as will be further described below.

Figure 15:
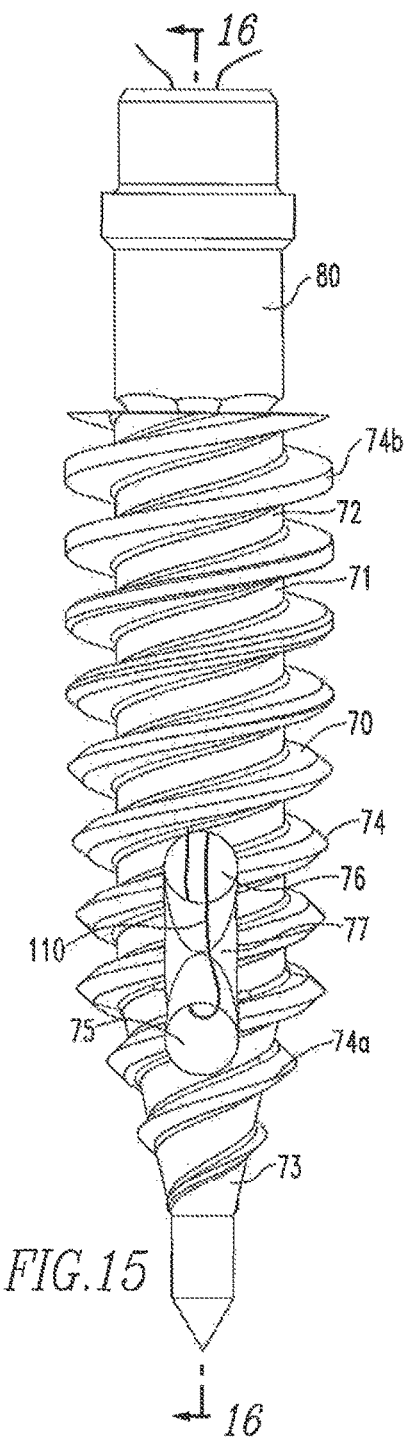
FIG. 15 shows a side view of the suture anchor of FIG. 13 and a delivery device coupled to the suture anchor.

As shown in FIGS. 15 and 21, flexible members 110,120, such as a suture, extend around the bridges 77,97 of the anchors 70,90 and through the cannulations 83,103 of the delivery devices 80,100.

Prior to insertion of any of anchors 10,60,70,90, the anchor dilator 200 may be used to prep the bone for insertion of the anchor 10,60,70,90. The dilator 200 includes a shaft 201, a handle 202 coupled to a proximal portion 201a of the shaft 201, and a dilating portion 203 coupled to a distal portion 201b of the shaft 201. The dilating portion 203 has a body 203a similar to the body 71,91 of each of anchors 70,90 and a thread profile similar to the thread profile of anchors 10,60,70,90. During tissue repair, a hole is made in bone by inserting the dilating portion 203 into the bone in an axial and rotational motion such that the user may strike the handle 202 to insert the pointed distal end 203b and then rotate the dilator 200 to insert the rest of the dilating portion 203. The dilating portion 203 is then removed from the bone and one of the anchors 10,60 may be inserted into the hole similar to the method described above for FIGS. 8 and 9 or one of the anchors 70,90 may be inserted into the hole in a manner similar to the manner of inserting the dilating portion of the anchor dilator, as described above. After insertion of one of the anchors 10,60,70,90 into the hole, tissue repair is completed in a manner similar to the method described above for FIGS. 8 and 9.

Similar to anchor dilator 200, anchor dilator 300, shown in FIGS. 26 and 27, may be used to prep the bone for insertion of the anchor 10,60,70,90. The dilator 300 includes a shall 301, a handle 302 coupled to a proximal portion 301a of the shaft 301, and a dilating portion 303 coupled to a distal portion 301b of the shaft 301. The dilating portion 303 has a body 303a having a threaded first portion 303b and a non-threaded second portion 303c. The threaded first portion 303b has a thread profile similar to the thread profile of anchors 10,60,70,90. During tissue repair, a hole is made in bone by axially inserting the non-threaded second portion 303c into bone, via tapping of the handle 302, until the entire second portion 303c is inserted into the bone. The user then rotates the handle 302 to insert the entire first portion into the bone. The dilating portion 303 is then removed from the bone and one of the anchors 10,60,70,90 may be inserted into the hole. After insertion of one of the anchors 10,60, 70,90 into the hole, tissue repair is completed in a manner similar to the method described above for FIGS. 8 and 9.

For the purposes of this disclosure, anchors 70,90 are made from a metal material, such as titanium. However, other materials could be used to make each of the anchors 10,60,70,90. Anchors 70,90 and their features may be formed from a machining process or other known processes. The delivery devices 80,100 are made from a metal material via a machining process or other known process. The devices 80,100 may be made from another material that would allow the devices 80,100 to withstand the forces applied to the devices 80,100 during insertion of the anchors 10,60,70,90. The anchor dilator 200,300 is made from a metal material, however, other materials that would allow the dilator 200,300 to withstand the forces applied to the dilator 200,300 during insertion of portion 203,303 into bone may be used. The dilator 200,300 may be made from a machining process or other known process. The delivery devices 20,80,100 include handles opposite the distal ends 2101,101 of the devices 20,80,100.

As various modifications could be made to the exemplary embodiments, as described, above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A delivery device and anchor combination, the combination comprising:
   a delivery device comprising an elongate shaft and a handle coupled to a proximal portion of the shaft, a distal portion of the shaft comprising a polygonal end including at least one prong extending from the end; and
   an anchor comprising:
      an anchor body including a proximal end, a tapered distal end, and a central axis extending between the proximal and distal ends;
      at least one through hole oriented transverse to the central axis of the anchor body;
      a cannulation extending along the central axis of the anchor body having a polygonal shape corresponding the polygonal end of the distal portion of the shaft, a distal portion of the cannulation extending around the at least one through hole to form at least one slot; and
      a suture bridge extending from the at least one through hole toward the distal end of the anchor body;
   wherein the anchor is positioned on the distal portion of the shaft such that the at least one prong of the shaft engages the at least one slot of the anchor body.

2. The combination of claim 1, wherein the anchor body includes threads along at least a partial length of the anchor body, wherein a profile of the threads near the distal end of the anchor body has a first shape and a profile of the threads near the proximal end of the anchor body has a second shape different from the first shape.

3. The combination of claim 1, wherein the at least one prong of the delivery device is two prongs and the at least one slot of the anchor is two slots.

4. The combination of claim 3, wherein the polygonal end of the shaft of the delivery device is a square-shaped end, and the two prongs are located at opposite corners of the square-shaped end.

5. The combination of claim 1, wherein the polygonal end of the shaft of the delivery device is a square-shaped end and the polygonal shape of the cannulation of the anchor body is a square shape.

6. The combination of claim 5, wherein two corners of the cannulation of the anchor are aligned with the at least one through hole, and another two corners of the cannulation are not aligned with the at least one through hole.

7. The combination of claim 1, wherein a distal end of the at least one slot extends beyond a distal end of the at least one through hole.

8. The combination of claim 1, wherein the at least one through hole includes a first through hole and a second through hole, and the suture bridge extends between the first through hole and the second through hole.

* * * * *